(12) United States Patent
Juhl

(10) Patent No.: US 8,004,670 B2
(45) Date of Patent: Aug. 23, 2011

(54) APPARATUS AND METHOD FOR SPECTROPHOTOMETRIC ANALYSIS

(75) Inventor: Henrik V Juhl, Roskilde (DK)

(73) Assignee: Foss Analytical A/S, Hillerod (DK)

( * ) Notice: Subject to any disclaimer, the term of this patent is extended or adjusted under 35 U.S.C. 154(b) by 391 days.

(21) Appl. No.: 11/992,385

(22) PCT Filed: Nov. 13, 2006

(86) PCT No.: PCT/EP2006/068392
§ 371 (c)(1),
(2), (4) Date: May 9, 2008

(87) PCT Pub. No.: WO2007/065772
PCT Pub. Date: Jun. 14, 2007

(65) Prior Publication Data
US 2009/0290153 A1   Nov. 26, 2009

(30) Foreign Application Priority Data
Dec. 5, 2005 (EP) .................................... 05111684

(51) Int. Cl.
*G01N 1/10* (2006.01)
(52) U.S. Cl. ........................................ 356/246; 356/319
(58) Field of Classification Search .......... 356/244–246, 356/36–42; 422/82.05, 82.09; 250/428–438; 435/288.5
See application file for complete search history.

(56) References Cited

U.S. PATENT DOCUMENTS

| | | | |
|---|---|---|---|
| 3,194,111 A | 7/1965 | Saunders | |
| 4,980,551 A | 12/1990 | Wong | |
| 5,284,623 A * | 2/1994 | Yamori et al. | 422/99 |
| 5,309,213 A | 5/1994 | Desjardins et al. | |
| 5,602,647 A * | 2/1997 | Xu et al. | 356/435 |
| 5,750,998 A | 5/1998 | Goldman | |
| 6,426,213 B1 * | 7/2002 | Eisenson | 435/288.7 |
| 6,628,382 B2 | 9/2003 | Robertson | |
| 6,809,826 B2 | 10/2004 | Robertson | |
| 2008/0252881 A1 * | 10/2008 | Yakimoski et al. | 356/246 |

FOREIGN PATENT DOCUMENTS

| | | |
|---|---|---|
| EP | 0706043 | 10/1995 |
| EP | 1102057 | 11/1999 |
| GB | 796745 | 1/1957 |
| WO | WO 97/05472 | 2/1997 |
| WO | WO 97/43619 | 11/1997 |

* cited by examiner

*Primary Examiner* — Tarifur Chowdhury
*Assistant Examiner* — Tara S Pajoohi
(74) *Attorney, Agent, or Firm* — Harness, Dickey & Pierce, PLC

(57) ABSTRACT

An apparatus for spectrophotometric analysis comprises a sample reception surface, which is arranged to receive a sample to be analysed, and a sample contacting surface, which is moveable in relation to the sample reception surface such that it may be brought to a first position, where the surfaces are sufficiently far apart to allow the sample to be placed on the sample reception surface, and a second position, where the sample contacting surface makes contact with the sample and compresses the sample. The apparatus further comprises a sample thickness controller, which is arranged to control the distance between the sample reception surface and the sample contacting surface in the second position of the sample contacting surface, such that a sample thickness between the surfaces may be shifted for obtaining at least two measurements of the sample at different optical path lengths through the sample.

5 Claims, 2 Drawing Sheets

APPARATUS AND METHOD FOR SPECTROPHOTOMETRIC ANALYSIS

PRIORITY STATEMENT

This application is the National Phase under 35 U.S.C. §371 of PCT International Application No. PCT/EP2006/068392 which has an International filing date of Nov. 13, 2006, which designated the United States of America and which claims priority on European Patent Application number 05111684.6 filed Dec. 5, 2005.

TECHNICAL FIELD

The present invention relates to an apparatus and a method for spectrophotometric analysis.

BACKGROUND OF THE INVENTION

It is well known to provide a spectrophotometer for the quantitative and/or qualitative determination of substances of interest in a test sample material, particularly a solution. Such a spectrophotometer detects electro-magnetic energy, typically optical energy, at one or more defined wavelengths after its interaction with a test sample retained in a sample holder, such as a cell or cuvette. This spectrophotometer device may be configured to operate in one or more of the well known transmission, reflectance or transflectance modes and may, for example, comprise a dispersion element monochromator or may, for example, be configured as an interferometer, such as a Fourier Transform interferometer.

A sample is conventionally poured into the cell or cuvette. When a spectrophotometric measurement is to be performed over a short path length, such as for samples having large absorption for the wavelength used, the sample may need to be pumped into the cell or cuvette. Where a short path length is used, the path length need to be stable and accurately controlled, since a small difference in path length will now represent a greater percentage change in the path length and will therefore greatly affect the measurement results.

It is also known from for example U.S. Pat. No. 5,602,647 to provide an optical spectrophotometer in which a sample holder has a variable internal optical path length. In this spectrophotometer the path length is varied in order to optimize the intensity of a particular wavelength detected. The spectrophotometer is configured to make the quantitative and/or qualitative determination based on the intensity of transmitted optical radiation and the values of the optical path length at peak intensity positions. In this spectrophotometer, it is very important that the variable path length can be accurately controlled. An incorrect path length used for quantitative determination will result in an incorrect result from the measurements. Thus, the variation of the optical path length may introduce faults in the results, if the path length is not accurately controlled.

U.S. Pat. No. 6,628,382 discloses another apparatus for spectrophotometry on extremely small liquid samples. The apparatus comprises two anvil surfaces. One of the surfaces may be swung clear of the other such that the surfaces may be easily cleaned and a sample may be easily applied. A liquid drop is placed on a surface, and the other surface is brought in contact with the drop. Thereafter, the surfaces are drawn apart so that the sample is pulled into a column. In this position, the spectrophotometric measurement is performed. Two measurements may alternatively be performed at two different path lengths. This is suitable where the accuracy of the path difference for a small path difference can be better determined than the absolute full optical path. According to U.S. Pat. No. 6,628,382, the optical path length must still be very accurately controlled.

GB 796,745 discloses a variable path-length absorption cuvette for liquids having a sample contacting surface and a sample receiving surface that are relatively slidable in order to vary an optical path-length between the two surfaces. The sliding mount is of a relatively complex and hence expensive construction, arranged to ensure that the two surfaces remain accurately parallel to one another as the path-length is varied.

SUMMARY OF THE INVENTION

It is an object of the present invention to provide a device and method for spectrophotometric analysis, which allows simple presentation of a sample to the spectrophotometer. It is another object of the invention to provide a spectrophotometer that is designed to easily perform measurements on different path lengths of a sample.

These and other objects of the invention are at least partly achieved by means of a device according to claim 1 and a method according to claim 8.

Thus, according to a first aspect of the invention, there is provided an apparatus for spectrophotometric analysis. The apparatus comprises a sample reception surface, which is arranged to receive a sample to be analysed, and a sample contacting surface, which is arranged together with the sample reception surface for their relative movement such that they may be brought to a first relative position, where the surfaces are sufficiently spaced apart to allow the sample to be placed on the sample reception surface without contacting the sample contacting surface, and a second relative position, where the sample contacting surface makes contact with the sample on the sample reception surface to effect a squeezing of the sample therebetween. The apparatus further comprises a sample thickness controller, which is arranged to control the distance between the sample reception surface and the sample contacting surface in the second position of the sample contacting surface, such that a sample thickness between the surfaces may be shifted for obtaining at least two measurements of the sample at different optical path lengths through the sample.

According to the first aspect of the invention, a sample reception surface may be presented so as to allow access to the surface. This implies that a sample may be placed directly on the surface, without the need of pumping the sample into a sample holder. This is a simple and cheap solution, since no flow system with associated pumps and tubes is needed. Further, the access to the sample reception and sample contacting surfaces also provides a possibility to easily clean the surfaces. Thus, maintenance of the apparatus is easily upheld. Consequently, the possibility to move the sample contacting surface apart from the sample reception surface whilst the two surfaces remain physically connected to one another makes the apparatus user-friendly.

The sample thickness controller sets the path length within a squeezed sample. Thus, the apparatus enables the path length to be set directly in a position where the sample reception and sample contacting surfaces have both been brought in contact with the sample. This makes the apparatus simple to use and the sample thickness controller may act instantly to set the path length when the sample contacting surface is approaching the sample reception surface. This also implies that the sample thickness controller may be implemented in a simple mechanical construction merely needing to hold the sample reception surface and the sample contacting surface at different distances from each other.

Further, the invention is partly based on the insight that performing two measurements on a sample with two different path lengths may be used for determining contents of a sample in a clever way. By employing a ratio of transmitted intensities at two different path lengths through the sample and performing suitable pre-processing of this ratio, such as standard normal variant (SNV) transformation or multiplicative scatter correction (MSC), it is not necessary to know the exact path length in the measurements. The pre-processed spectrum is not dependent of the path length at which the spectra were measured. This insight provides a possibility to determine contents even if the measurements are not performed at the exact path lengths intended. Therefore, the apparatus does not need to control the sample thickness very accurately for the measurements at different path lengths. This implies that the requirements on the sample thickness controller to control the sample thickness are not extreme. Further, it enables the sample thickness controller to shift path lengths within a squeezed sample having a small path length, even though an inaccuracy in the set path length would give a large relative error.

According to an embodiment, the sample contacting surface is hingedly connected to the sample reception surface. This implies that the sample contacting surface may easily be moved between the first and second positions. The sample contacting surface may be manually handled to turn the sample contacting surface around the hinge to move the surface. Also, since the sample thickness controller need not extremely accurately set the path length through the sample, it is irrelevant that the sample contacting surface is not moved in a direction along a normal to the surfaces.

The sample thickness controller may comprise a protrusion, which extends from one of the sample reception surface or the sample contacting surface, wherein the distance between the sample reception surface and the sample contacting surface is controlled by the distance the protrusion extends from the surface. The protrusion will thus keep the sample contacting surface a certain distance apart from the sample reception surface, this distance being controlled by the extent of protrusion from one surface. The sample thickness controller may additionally comprise a motor for controlling the distance the protrusion extends from the surface.

The sample thickness controller may be arranged to control the lowering of the sample contacting surface towards the second position such that the sample contacting surface is slowly brought towards the second position. This ensures that the entire sample contacting surface may come in contact with the sample. For example, if the sample is liquid, the entire sample contacting surface may be wetted by the sample contacting surface slowly making contact with the sample. Further, the sample contacting surface may be manually brought towards the second position, whereas the sample thickness controller controls the final lowering of the sample contacting surface.

The sample thickness controller may be arranged to shift the sample thickness in a range of 10-50 μm, preferably 15-45 μm. This is suitable for measurements to be performed on highly absorbing samples. The invention is especially suitable for use in measurements on such short path lengths, since these path lengths have traditionally been provided by complex cuvettes with extreme accuracy in the provided path length. These cuvettes have been associated with pumps for presenting a sample into the cuvette. Thus, the invention provides a much simpler and cheaper apparatus for performing measurements on such short path lengths.

The apparatus may further comprise an arithmetic unit, which is arranged to receive outputs from the at least two measurements at the different path lengths and which is adapted to calculate a value dependent on the ratio of received outputs at two path lengths for a same wavelength used in the measurements and to generate therefrom one or both a quantitative and a qualitative indication of a substance of interest within the sample.

By dividing the intensities of detected light of the same wavelength after they have traversed two different paths through the same sample then intensity related instabilities are removed. This implies that the measurements are not affected by random temporal intensity drift in the spectrophotometer, which may be caused by unstable operating conditions, such as variations in the temperature of the instrument. The removal of the intensity related instabilities implies that there is no need for regularly performing measurements on a calibration sample for so-called "zero-setting" of the spectrophotometer.

Moreover, as described above, by arranging for the arithmetic unit to perform the ratio calculations, variations in path lengths through the sample will not affect the results of the measurement.

A second aspect of the invention provides a method for spectrophotometric analysis of a sample. The method comprises placing the sample on a sample reception surface and lowering a sample contacting surface in relation to the sample reception surface such that it is brought to a position, where the sample contacting surface makes contact with the sample placed on the sample reception surface and squeezes the sample between the sample reception surface and the sample contacting surface. The method further comprises controlling a first path length through the sample in the squeezed sample, performing a first measurement on the sample with the first path length, changing the path length through the sample in the squeezed sample to a second path length, and performing a second measurement on the sample with the second path length.

The method provides a user-friendly method of performing spectrophotometric analysis, where a sample may be presented in a simple way to the spectrophotometer and the path length of the sample is easily controlled.

A third aspect of the invention provides a sample holder for a spectrophotometric analysis apparatus. The sample holder comprises a sample reception surface having a first light transmitting region, and a sample contacting surface having a second light transmitting region, wherein the surfaces are connected for relative movement between a first position, at which the connected surfaces are spaced apart to allow a sample to be received at the first light transmitting region, and a second position, at which the first and second light transmitting regions maintain intimate contact with and squeeze the received sample while being moveable to change the thickness of the sample between the light transmitting regions for obtaining different optical path lengths through the squeezed sample.

This sample holder may be a separate unit, which may be connected into a spectrophotometric analysis apparatus for performing an analysis on a sample. Alternatively, the sample holder may be an integrated unit in the analysis apparatus.

BRIEF DESCRIPTION OF THE DRAWINGS

The invention will now by way of example be described in further detail with reference to the accompanying drawings.

DETAILED DESCRIPTION OF PREFERRED EMBODIMENTS

Figure 1:
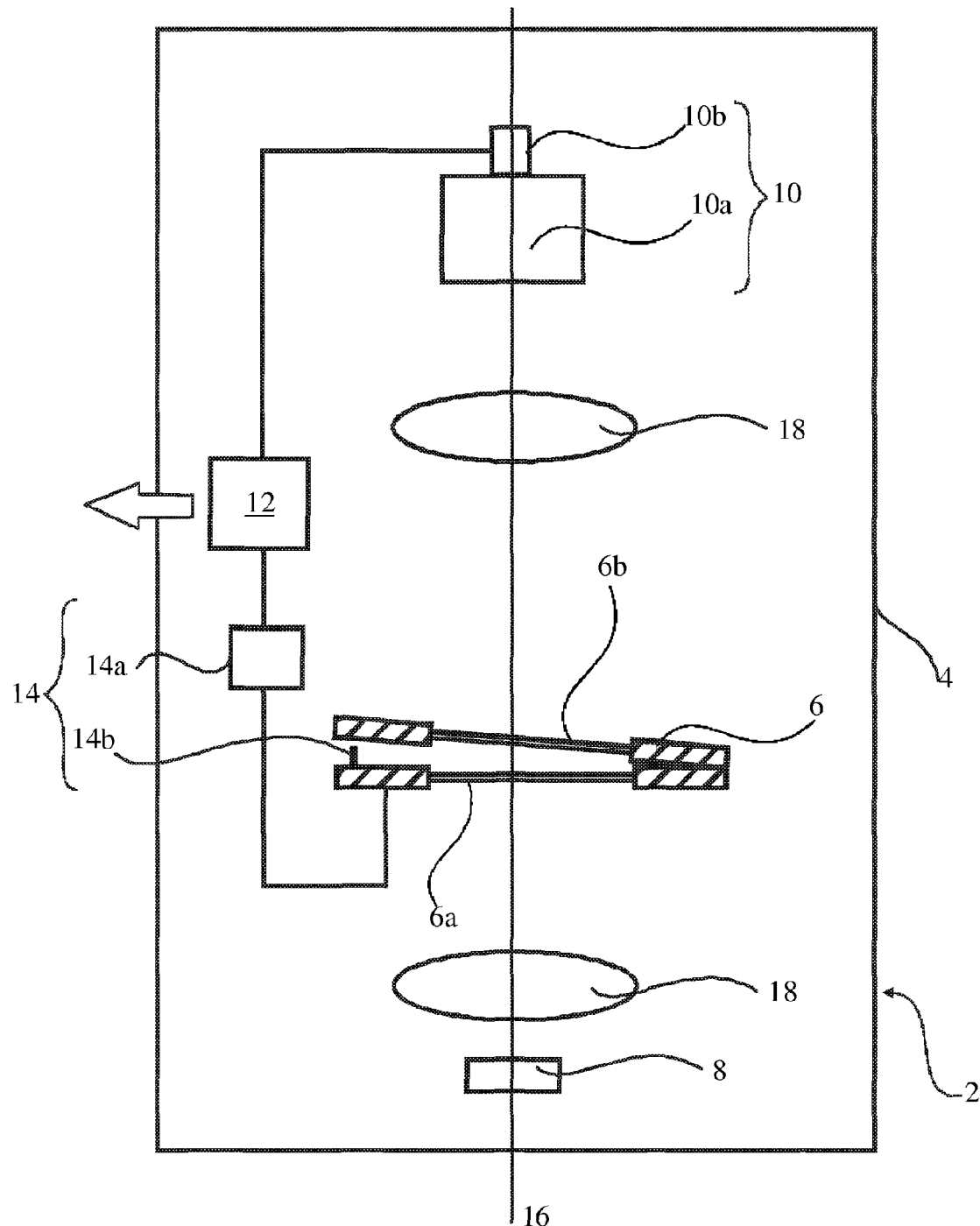
FIG. 1 is a schematic view of the components of an apparatus for spectrophotometric analysis according to an embodiment of the invention.

Referring now to FIG. 1, a spectrophotometer 2 according to an embodiment of the invention will now be described. The spectrophotometer 2 comprises a housing 4, in which all parts of the spectrophotometer 2 are arranged. Thus, all optical components of the spectrophotometer 2 are arranged within the housing 4. The housing 4 protects the optical components and prevents the optical set-up from becoming distorted.

The spectrophotometer 2 has a display (not shown) for presenting results to a user. The spectrophotometer also has a sample holder 6, which provides presenting a sample to the spectrophotometer 2 in a simple way.

Now, the optical set-up of the spectrophotometer 2 will be explained. The spectrophotometer 2 comprises a sample holder 6; a polychromatic light source 8, a detection arrangement 10; an arithmetic unit 12 and a control unit 14a of a sample thickness controller 14 for setting a sample thickness. In the present example the source 8, sample holder 6 and detection arrangement 10 are relatively disposed so that in use light from the source 8 passes along an optical axis 16 to be transmitted through opposing surfaces 6a, 6b of the sample holder 6 before being detected by the detection arrangement 10. Focussing optics 18, here shown as a pair of lenses, may be provided and employed in a known manner to form the desired light beam shape from the source 8, through the sample holder 6 and to the detection arrangement 10.

The sample holder 6 of the present embodiment is configured with the opposing surfaces 6a, 6b in a direction along the optical axis 16 formed in whole or in part of light transmitting material and being movable relative to one another, as will be further described below. The control unit 14a is operably connected to one or both opposing surfaces 6a, 6b in order to exert a force thereon so as to change their relative separation and hence the optical path length through the sample cell 6.

The polychromatic light source 8 is here configured to generate and emit all of the specific wavelengths of interest simultaneously. According to one embodiment, the polychromatic light source 8 is arranged to emit infrared radiation. To complement this, the detection arrangement 10 is here comprised of a spectrometer 10a and an associated photo-detector 10b. These elements 10a, 10b are mutually configured in a known manner so as to be able to generate a wavelength dependent transmission spectrum of sample material within the sample cell 6.

The arithmetic unit 12 is operably connected to an output of the photo-detector 10b. The arithmetic unit 12 is configured to receive and preferably to store a so generated transmission spectrum at a plurality, being preferably least two, different separations of the two surfaces 6a, 6b. The unit 12 may be configured to store the spectra as indicated by an output from the unit 12 and may comprise a plurality of separate but interconnected units rather than the single functional unit 12 that is illustrated in the present embodiment.

In operation the arithmetic unit 12 of the present embodiment records spectral data from the detection arrangement 10 corresponding to a first separation of the surfaces 6a, 6b. The sample thickness controller 14 is then operated to change the separation between the surfaces 6a, 6b and the arithmetic unit 12 records spectral data from the detection arrangement 10 corresponding to a second, different, separation of the surfaces 6a, 6b. In this manner intensity values for light from the polychromatic source 8 which is transmitted through the sample material, indexed to their wavelengths, are available to the arithmetic unit 12 for at least two different optical paths through the sample material. The arithmetic unit 12 is configured to make a quantitative or a qualitative determination of the presence of a substance of interest within the sample material based on calculations of the ratio of the thus obtained intensity values at the same wavelengths for each of the two different path lengths. The unit 12 is further configured to then output an indication of the so made determination. This may, for example, be in the form of a quantitative measure of the substance of interest or may be, for example a qualitative indication of the presence of the substance of interest within the sample.

More specifically the arithmetic unit 12 is configured to make use of methodology encapsulated by the following equations when carrying out the determinations:

The intensity of light of wavelength $\lambda$, ($I_{1\lambda}$) that is received at the detector 10b after traversing a path length $b_1$ through a sample having an absorption coefficient $a_\lambda$, (includes both sample and holder absorption coefficients) and containing a concentration, C, of a substance of interest may be expressed according to the known equation:

$$I_{1\lambda} = I_{0\lambda} \exp(a_\lambda \cdot C \cdot b_1) \quad (1)$$

Where $I_{0\lambda}$ is the intensity of the light of wavelength $\lambda$ incident at the surface 6a of the holder 6.

Similarly for a shorter path length $b_2$ the intensity received by the detector 10b at the same wavelength $\lambda$ may be expressed as:

$$I_{2\lambda} = I_{0\lambda} \exp(a_\lambda \cdot C \cdot b_2) \quad (2)$$

Using these two equations (1) and (2) representing the determined intensities, the wavelength dependent absorbance $A_\lambda$, may be expressed as:

$$A_\lambda = \log(I_{2\lambda}/I_{1\lambda}) = a_\lambda \cdot C \cdot (b_1 - b_2) \quad (3)$$

Thus in a most simple configuration the arithmetic unit 12 may be configured to determine the concentration C from equation (3) and from a knowledge of the two path lengths $b_1$ and $b_2$ (at least their difference); the associated detected intensities $I_{1\lambda}$ and $I_{2\lambda}$, and the value of the absorption coefficient $a_\lambda$, at the wavelength(s), $\lambda$, of interest.

However, more commonly, the science of chemometrics may be applied to the problem in a generally known manner whereby multivariate statistical analysis is employed in order to produce a calibration algorithm which establishes a correlation of the absorbance, $A_\lambda$, to the concentration, C, of a substance of interest. As is well known, this involves the use of a set of "training" or calibration samples which are preferably selected to span the complete range of concentrations and substances likely to be of interest. It has been realised that performing suitable pre-processing of the ratio in equation (3), such as standard normal variant transformation, it is not necessary to know the exact path length in the measurements. The pre-processed spectrum using the standard normal variant transform is not dependent of the path length at which the spectra were measured. Thus, it will be appreciated that in this manner the actual optical path or path difference for any test sample need not be known in order for the arithmetic unit 12 to make a prediction regarding a particular one or more substances of interest.

Figure 2:
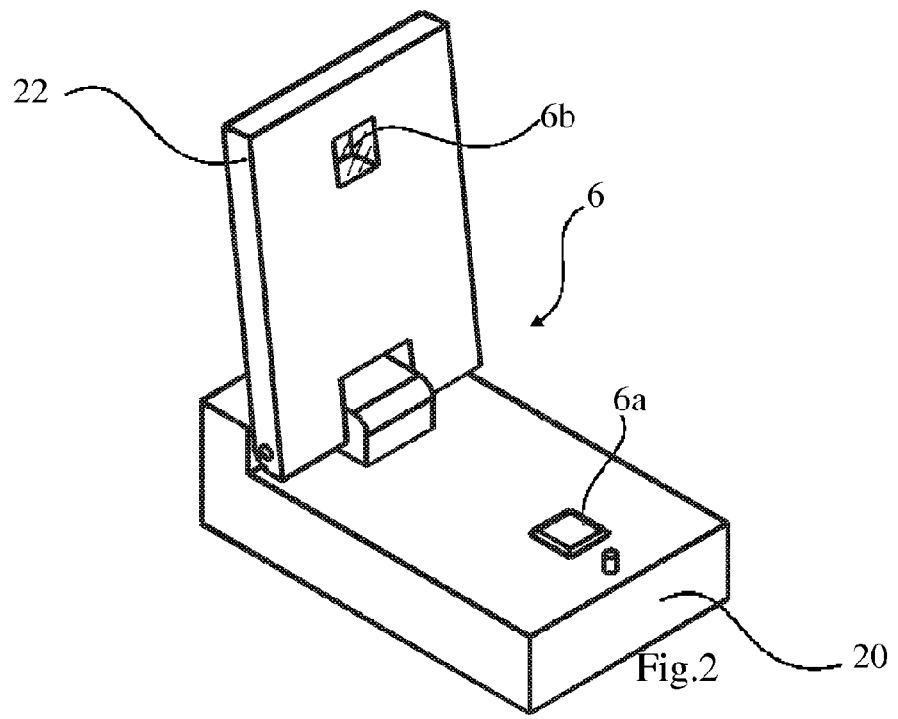
FIG. 2 is a perspective view of a sample holder of the apparatus of FIG. 1 illustrating a sample contacting surface being spaced apart from a sample reception surface for allowing a sample to be applied on the sample reception surface.
Figure 3:
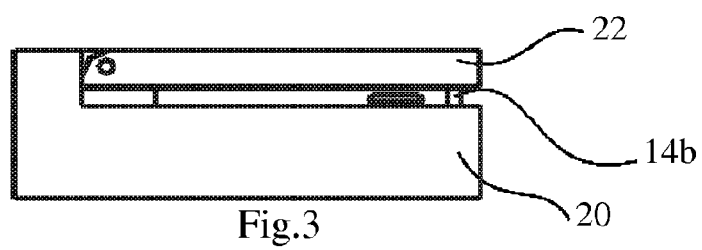
FIG. 3 is a side view of the sample holder illustrating the sample contacting surface being brought in contact with the sample for performing spectrophotometric measurements.
Figure 4:
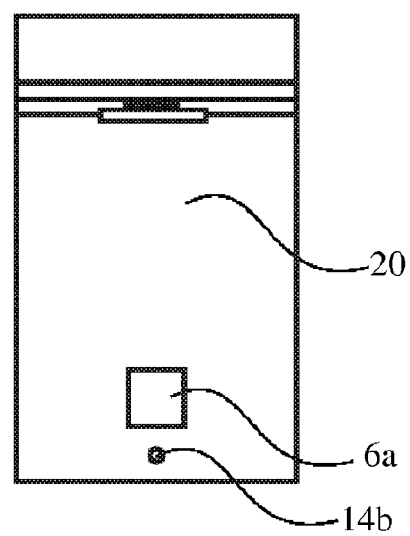
FIG. 4 is a plan view of the sample reception surface illustrating protrusions for controlling the distance between the sample reception surface and the sample contacting surface.

Referring now to FIGS. 2-4, the sample holder 6 of the spectrophotometer 2 will now be described in further detail.

The sample holder 6 comprises a sample reception surface 6a and a sample contacting surface 6b. These two surfaces 6a, 6b are moveable in relation to each other. The sample contacting surface 6b constitutes a face of a lid 22, which is hingedly connected to a bottom 20. The sample reception surface 6a constitutes a face of the bottom 20. At least a portion of the surfaces 6a, 6b that make contact with a sample are formed of a light transmitting material providing windows for allowing light to enter and exit the sample. The light emitted by the source 8 is directed through one of the surface windows and the light transmitted through the sample and the other surface window is directed to the detector 10. The source 8 or the detector 10 is arranged inside the lid 22 in order to merely require electronic couplings into the lid 22 and avoiding coupling the optical path into or out of the lid 22.

The lid 22 turns about the hinge for shifting between an open and a closed state of the sample holder 6. The lid 22 may be manually manoeuvred between the open and closed states by gripping the outer part of the lid 22 farthest away from the hinge. The sample holder 6 is shown in FIG. 2 in its open state. As can be seen, the sample reception surface 6a and the sample contacting surface 6b are far apart in this open state, where the lid 22 has been opened approximately 90 degrees. This implies that a user is provided access to the surfaces 6a, 6b, such that the surfaces 6a, 6b may easily be cleaned. Further, a sample may easily be applied to the sample reception surface 6a. Typically, a sample is applied in the form of a liquid or viscous material.

When a sample has been applied to the sample reception surface 6a, the lid 22 is closed. The lid 22 may be closed manually. When the lid 22 is close to the bottom 20, it will make contact with an adjustable protrusion 14b, which controls the separation of the surfaces 6a, 6b. The protrusion 14b may initially extend sufficiently to prevent the sample contacting surface 6b to make contact with the sample. This implies that the user will not bring the sample contacting surface 6b in contact with the sample, whereby the contacting may be accurately controlled. When the sample contacting surface 6b contacts the protrusion 14b, the control unit 14a will control the distance that the protrusion 14b extends from the bottom 20 for adjusting the separation of the sample contacting surface 6b from the sample reception surface 6a. In this way, the sample contacting surface 6b may be slowly lowered towards the sample reception surface 6a such that the sample applied on the sample reception surface 6a is allowed to wet the entire optical window on the sample contacting surface 6b. In FIG. 3, the sample holder 6 is shown in its closed state.

Now, when the sample is squeezed and both surfaces 6a, 6b are in contact with the sample, a spectrophotometric measurement may be performed. The sample thickness controller 14 sets a first distance between the surfaces 6a, 6b for providing a first path length through the sample. After a first spectrophotometric measurement has been performed, the sample thickness controller 14 sets a second distance between the surfaces 6a, 6b for providing a second path length through the sample, and a second spectrophotometric measurement is performed. The sample thickness controller 14 sets the distances by adjusting the distance that the adjustable protrusion 14b protrudes from the bottom 20. For a measurement using infrared radiation, the first distance may be set to about 40 μm and the second distance may be set to about 15 μm.

As shown in FIG. 4, the adjustable protrusion 14b extends from a portion of the bottom 20 at an edge farthest away from the hinge. The adjustable protrusion 14b may be a screw or a tap and the extension of the adjustable protrusion 14b may be controlled by means of a motor (not shown). The motor engages with the protrusion 14b for setting the position of the protrusion 14b. The control unit 14a controls the motor to set the appropriate extension of the protrusion 14b from the bottom 20.

The spectrophotometer described above is suitable for analysis of liquids, such as beverages, edible oils or the like. The spectrophotometer may also be used for analysis of viscous or semi-fluid substances, such as yoghurts, sour creams and the like.

It should be emphasized that the preferred embodiments described herein are in no way limiting and that many alternative embodiments are possible within the scope of protection defined by the appended claims.

For example, the sample reception surface and the sample contacting surface may alternatively be moveable along a direction perpendicular to the surfaces. This implies that the distance between the surfaces may be more accurately controlled, since the separation between the surfaces is equal over the entire faces. However, the sample contacting surface may need to be brought a substantial distance away from the sample reception surface in order to allow access to the surfaces for sample presentation and cleaning.

As a further alternative, the sample holder 6 may be arranged as a detachable unit that may be completely detached from the spectrophotometer 2 for applying a sample to the sample reception surface 6a. The sample holder 6 may then be fitted to the spectrophotometer 2 for guiding light through the sample. The source 8 and detection arrangement 10 are preferably not arranged in the detachable unit, so that light is merely guided into the sample holder 6 through the sample and out of the sample holder 6 towards the detection arrangement 10. The sample holder 6 and the spectrophotometer 2 comprise mutually engagable means, such as protrusions and corresponding recesses. This implies that the relative position between the sample holder 6 and the spectrophotometer 2 may be well-defined in order to ensure that the optical path through the sample holder 6 complies with the optical path of the spectrophotometer 2.

It will be appreciated that the sample thickness controller 14 may be configured to operate in a manner so as to provide three or more different separations of the two faces 6a, 6b at which spectra are to be recorded and stored by the arithmetic unit 12. In such case, the arithmetic unit 12 may be advantageously configured to derive a plurality of values indicative of the substance of interest in a same sample from intensity values obtained at different pairs of path lengths and using equation (3) or the chemometrics described above. These so derived plurality of values may be simply combined to provide an average value quantitatively indicating the presence of the substance of interest or may be combined, such as by appropriately weighting each value, in order to provide such a quantitative indication.

It will be appreciated by those skilled in the art that the sample holder 6 may be incorporated into other spectrophotometer arrangements, such as into an optical path of an arm of a known Fourier Transform Infra-red (FTIR) spectrophotometer arrangement, without departing from the invention as claimed.

It will be further appreciated that radiation in many different wavelength regions may be employed, such as ultra-violet, visible, near infrared or infrared light or any combination thereof.

The invention claimed is:

1. A sample holder for a spectrophotometric analysis apparatus, said sample holder comprising:
   a sample reception surface having a first light transmitting region, and
   a sample contacting surface having a second light transmitting region,
      wherein the surfaces are connected for relative movement between a first position, at which the connected surfaces are spaced apart to receive a sample at the first light transmitting region, and a second position, at which the first and second light transmitting regions maintain intimate contact with and squeeze the received sample, the sample reception surface and the sample contacting surface being moveable to change a thickness of the sample between the light transmitting regions for obtaining different optical path lengths through the sample, and
   a sample thickness controller, which is arranged to control the distance between the sample reception surface and the sample contacting surface in the second position such that a sample thickness between the surfaces may be changed for obtaining at least two measurements of the sample at different optical path lengths through the sample, wherein the sample contacting surface is hingedly connected to the sample reception surface,
   wherein the sample thickness controller includes an adjustable protrusion, which extends from one of the sample reception surface or the sample contacting surface, whereby in the second position the distance between the sample reception surface and the sample contacting surface is controlled by adjusting a distance the protrusion extends from the associated surface.

2. The sample holder according to claim 1, wherein the sample thickness controller further comprises a control unit configured to automatically control the distance the protrusion extends from the associated surface.

3. The sample holder according to claim 2, wherein the sample thickness controller is arranged to control the movement of the sample contacting surface towards the second position such that the sample contacting surface is slowly brought towards the second position.

4. A method for spectrophotometric analysis of a sample, said method comprising:
   placing the sample on a sample reception surface of a sample holder according to claim 1,
   lowering a sample contacting surface in relation to the sample reception surface such that the sample contacting surface is brought to a position, wherein the sample contacting surface makes contact with the sample placed on the sample reception surface and squeezes the sample between the sample reception surface and the sample contacting surface, controlling a separation of the sample reception surface and the sample contacting surface to provide a first path length through the squeezed sample,
   performing a first measurement on the sample with the first path length to determine a first wavelength dependent intensity of light traversing the first path length,
   controlling the separation of the sample reception surface and the sample contacting surface to change the path length through the squeezed sample to a second path length,
   performing a second measurement on the sample with the second path length to determine a second wavelength dependent intensity of light traversing the second path length, and
   generating in an arithmetic unit at least one of a quantitative and a qualitative indication of a substance of interest within the sample dependent on a ratio of intensities at the first and the second path lengths for the same wavelength.

5. An apparatus for spectrophotometric analysis, said apparatus comprising:
   a detection arrangement optically coupled to internal a sample holder to perform spectrophotometric analysis of a sample held therein, wherein
      the sample holder is a sample holder as claimed in claim 1, and
      the apparatus further includes an arithmetic unit configured to receive outputs from the at least two measurements performed at the different path lengths and to calculate a value dependent on the ratio of received outputs at the two path lengths for a same wavelength and to generate therefrom one or both a quantitative and a qualitative indication of a substance of interest within the sample.

* * * * *

UNITED STATES PATENT AND TRADEMARK OFFICE
CERTIFICATE OF CORRECTION

PATENT NO. : 8,004,670 B2
APPLICATION NO. : 11/992385
DATED : August 23, 2011
INVENTOR(S) : Henrik V. Juhl Page 1 of 1

It is certified that error appears in the above-identified patent and that said Letters Patent is hereby corrected as shown below:

Title Page, Item (30) should read:

-- Foreign Application Priority Data

Dec. 5, 2005    (EP) ....................................... 05111684.6 --

Signed and Sealed this
Twenty-ninth Day of November, 2011

David J. Kappos
*Director of the United States Patent and Trademark Office*